US010206869B2

(12) United States Patent
Cattuzzato et al.

(10) Patent No.: US 10,206,869 B2
(45) Date of Patent: Feb. 19, 2019

(54) OBTAINING AN EXTRACT FROM BROWN ALGAE GAMETOPHYTES, AND USE OF SAID EXTRACT AS A COSMETIC ANTI-AGING ACTIVE PRINCIPLE

(71) Applicants: SOCIETE D'EXPLOITATION DE PRODUITS POUR LES INDUSTRIES CHIMIQUES SEPPIC, Paris (FR); BIOTECHMARINE, Quemper Guezennec (FR)

(72) Inventors: Laetitia Cattuzzato, Castres (FR); Sandy Dumont, Caucalieres (FR); Erwan Le Gelebart, Ploubazlanec (FR); Jerome Loeuil, Paris (FR)

(73) Assignees: SOCIETE D'EXPLOITATION DE PRODUITS POUR LES INDUSTRIES CHIMIQUES SEPPIC, Paris (FR); BIOTECHMARINE, Quemper Guezennec (FR)

( * ) Notice: Subject to any disclaimer, the term of this patent is extended or adjusted under 35 U.S.C. 154(b) by 0 days.

(21) Appl. No.: 15/553,018

(22) PCT Filed: Feb. 19, 2016

(86) PCT No.: PCT/FR2016/050389
§ 371 (c)(1),
(2) Date: Aug. 23, 2017

(87) PCT Pub. No.: WO2016/135400
PCT Pub. Date: Sep. 1, 2016

(65) Prior Publication Data
US 2018/0028437 A1 Feb. 1, 2018

(30) Foreign Application Priority Data
Feb. 24, 2015 (FR) ...................................... 15 51545

(51) Int. Cl.
A61K 36/00 (2006.01)
A61K 8/9711 (2017.01)
A61Q 19/08 (2006.01)
A61K 8/9706 (2017.01)

(52) U.S. Cl.
CPC .......... A61K 8/9711 (2017.08); A61K 8/9706 (2017.08); A61Q 19/08 (2013.01); A61K 2800/805 (2013.01)

(58) Field of Classification Search
CPC .................................................... A61K 36/00
See application file for complete search history.

(56) References Cited

U.S. PATENT DOCUMENTS

| 5,508,454 | A | 4/1996 | Brancq et al. |
| 6,326,033 | B1 | 12/2001 | Darmenton et al. |
| 2008/0089851 | A1 | 4/2008 | Mekideche |
| 2014/0087448 | A1 | 3/2014 | Mekideche |

FOREIGN PATENT DOCUMENTS

| EP | 0 971 683 A1 | 1/2000 |
| EP | 1 515 688 A2 | 3/2005 |
| FR | 2 761 595 A1 | 10/1998 |
| FR | 2837383 A1 | 9/2003 |
| FR | 2880803 A1 | 7/2006 |
| FR | 2948877 A1 | 2/2011 |
| JP | 02011256153 A * | 12/2011 |
| WO | 96/00719 A1 | 1/1996 |
| WO | 98/44902 A1 | 10/1998 |
| WO | 03/103616 A2 | 12/2003 |
| WO | 2015071477 A1 | 5/2015 |

OTHER PUBLICATIONS

FR Search Report, dated Aug. 19, 2015, from corresponding FR application No. 1551545.
Shin et al., "Chronic heat treatment causes skin wrinkle formation and oxidative damage in hairless mice", Mechanisms of Ageing and Development, 2012, pp. 92-98, vol. 133, No. 2-3.
Corstjens et al., "Prevention of oxidative damage that contributes to the loss of bioenergetic capacity in ageing skin", Experimental Gerontology, 2007, pp. 924-929, vol. 42, No. 9.
Kim et al., "Biological Activities and Potential Health Benefits of Fucoxanthin Derived from Marine Brown Algae", Advances in Food and Nutrition Research, 2011, pp. 111-128, Chapter 9, vol. 64.
Siefermann-Harms, "The light-harvesting and protective functions of carotenoids in photosynthetic membranes", Physiologia Plantarum, 1987, pp. 561-568, vol. 69, No. 3.
Goss et al., "Regulation and function of xanthophyll cycle-dependent photoprotection in algae", Photosynthesis Research, 2010, pp. 103-122, vol. 106, No. 1-2.
Mallick et al., "Reactive oxygen species: response of algal cells", Journal of Plant Physiology, 2000, pp. 183-193, vol. 157, No. 2.

(Continued)

Primary Examiner — Qiuwen Mi
(74) Attorney, Agent, or Firm — Young & Thompson

(57) ABSTRACT

Disclosed is a lipophilic extract of brown algae gametophytes obtained by the method including the following consecutive steps: —a Step A) for preparing a hydro-alcoholic suspension of gametophyte cells by mixing an aqueous suspension of brown algae gametophyte cells with at least one aliphatic alcohol including 1 to 4 carbon atoms; —a Step B) for mixing the hydro-alcoholic suspension of algae gametophyte cells, obtained in Step A), with at least one triglyceride from fatty acids that include 8 to 22 carbon atoms; —a Step C) for adding water to the multi-phase mixture obtained in Step B); and —a Step D) for isolating the lipophilic extract of brown algae gametophytes from the mixture obtained in Step C). Also disclosed are the cosmetic and pharmaceutical use of the extract.

18 Claims, No Drawings

(56) References Cited

OTHER PUBLICATIONS

D'Orazio et al., "Fucoxantin: A Treasure from the Sea", Marine Drugs, 2012, pp. 604-616, vol. 10.
May 27, 2016, International Search Report issued for related International Application No. PCT/FR2016/050389.
Gregory L. Rorrer, et al., Production of Hydroxy Fatty Acids by Cell Suspension Cultures of the Marine Brown Alga *Laminaria saccharina*, Phytochemistry, 1997, pp. 871-877, vol. 26, No. 5, Elsevier Science Ltd., Great Britain.
Valery M. Dembitsky, Betaine Ether-Linked Glycerolipids: Chemistry and Biology, Progress in Lipid Research, 1996, pp. 1-51, vol. 35, No. 1, Elsevier Science Ltd., Great Britain.

* cited by examiner

OBTAINING AN EXTRACT FROM BROWN ALGAE GAMETOPHYTES, AND USE OF SAID EXTRACT AS A COSMETIC ANTI-AGING ACTIVE PRINCIPLE

The subject of the present invention is a novel extract of brown alga gametophytes, the process for the preparation thereof, and also the use thereof as anti-aging agent for the skin of the human body, and the cosmetic, pharmaceutical, dermopharmaceutical compositions for tropical use containing same, intended to prevent the aging of the skin of the human body.

Since the human skin is the first thing noticed by others, improving the appearance thereof is often a preoccupation for humans. The skin reflects either a state of well-being, often associated with youth, or a state of fatigue and/or aging. Consumers of cosmetic products therefore seek solutions to alleviate and/or prevent visible signs associated with said aging.

This skin aging is observed in different cutaneous tissues and is characterised by metabolic, functional, cellular, architectural, and tissue alterations, leading to visible external effects such as the appearance and growth of wrinkles, a dull complexion and/or a lack of uniformity of this complexion (dyschromia) or else the modification of the texture and biomechanical properties of the skin.

This skin aging results on the one hand from factors unique to each individual (characteristics of the genetic heritage unique to each individual) and on the other hand from environmental factors. Among the environmental factors which may cause skin aging, there is the repeated and prolonged exposure to natural or artificial ultraviolet radiation (or photoaging), to atmospheric pollution or to cigarette smoke, and various oxidative, psychological, emotional and/or anxiety-related stresses.

Photoaging causes alterations to the skin at various levels, especially solar elastosis, which is characterized by profound modifications to the architecture and organization of the elastic fibers of the dermis, inducing the formation of very deep and pronounced wrinkles, a leathery appearance of the skin, that is to say stiff, cracked and brown, and also modifications of the mechanical properties of these fibers.

Confronted with these external attacks, the skin has its own defense systems, and especially systems for repairing damage caused to DNA by said external attacks. More particularly, these are antioxidant systems and systems for breaking down non-functional proteins. Among the antioxidant systems, two types of antioxidant elements are present in the organism: non-enzymatic elements, such as vitamin E and vitamin C, and enzymatic elements, such as superoxide dismutase and catalase. It has especially been demonstrated that some external elements such as ultraviolet A radiation and chronic thermal stress regulate catalase activity by reducing same, and that this was associated with the appearance of wrinkles [Shin et al., "Chronic heat treatment causes skin wrinkle formation and oxidative damage in hairless mice", 2012, Mech Ageing Dev, 133(2-3):92-8], [Corstjens et al., "Prevention of oxidative damage that contributes to the loss of bioenergetic capacity in ageing skin", 2007, Exp Gerontol, 42(9):924-9].

Skin aging has also been described as being associated with a lack of reactivity of the organism when confronted with the phenomenon of hypoxia (reduction in the level of oxygen). The cellular response to hypoxia involves the overexpression of the transcription factor HIF-1, composed of 2 subunits: alpha, the inducible subunit, and beta, the constitutively expressed subunit. This transcription factor enables the expression of other genes involved in adapting to hypoxia, leading to a metabolic change from the aerobic pathway to the anaerobic pathway, making it possible to preserve the amount of tissue oxygen, to angiogenesis, to cell survival and, in certain specific cases, to tumor induction. Thus, HIF-1 expression decreases during aging and a pseudo-hypoxic state arises within cells. Sirtuin 1 (SIRT-1) is an enzyme with a deacetylase function, which has been described as controlling the activity of the transcription factor HIF-1a. Through its activity, SIRT-1 is involved in regulating numerous biological processes by modifying the degree of acetylation of histones and/or transcription factors. Thus, its involvement in antioxidant protection (via induction of the catalase SOD) and in cell survival and longevity have been widely described.

The result of this is that overexpression of the transcription factor HIF-1 and/or of sirtuin 1 constitute means for preventing and/or treating aging of the skin of the human body, and more particularly for preventing and/or treating the visible effects of said aging, for example wrinkles, dull complexion, lack of uniformity of the complexion (dyschromia), and the stiffness of the skin of the human body, caused by natural aging or by prolonged exposure to the sun, and more particularly exposure to ultraviolet radiation, or exposure to oxidative stresses.

The class of the brown algae, also known as Phaeophyceae, is part of the phylum of the Ochrophytes. This phylum encompasses algae, the cells of which contain "supernumerary" carotenoid pigments, such as fucoxanthin, in addition to the chlorophyll pigments, chlorophyll a and c.

The class of the brown algae comprises the orders Ascoseirales, Asterocladales, Desmarestiales, Dictyotales, Dictyotophycidae, Discosporangiales, Discosporangiophycidae, Ectocarpales, Fucales, Fucophycidae, Ishigeales, Ishigeophycidae, Laminariales, Nemodermatales, Onslowiales, Phaeophyceae ordo incertae sedis, Phaeosiphoniellales, Ralfsiales, Scytothamnales, Sphacelariales, Sporochnales, Syringodermatales, and Tilopteridales.

All photosynthetic organisms use pigments to capture light energy, usually a form of chlorophyll. Standard chlorophyll is chlorophyll a, and it is essential for transferring the energy captured from light to the molecules which will use this energy. Most chlorophyll-containing organisms have other pigments to capture more light but the energy must always be transferred to the molecule of chlorophyll a.

Brown algae use several types of supernumerary pigments such as chlorophyll c and carotenoids. Phaeophyceae have large amounts of carotenoids in their plastids and these are the brown and yellow pigments which give them their characteristic brown color. The most important carotenoid pigment in brown algae is fucoxanthin which absorbs wavelengths from 450 to 580 nm.

Carotenoid pigments have an aliphatic or alicyclic structure. They are liposoluble which promotes their direct integration into certain membranes. For this reason, they can only be dissolved in water when they are bound to other molecules. Carotenoids are also referred to as accessory pigments because they must transfer the energy that they capture to chlorophyll a. These pigments are known to the general public through carotene which has given its name to this family of pigments.

Fucoxanthin, which belongs to the class of non-provitamin A carotenoids, is represented by the formula:

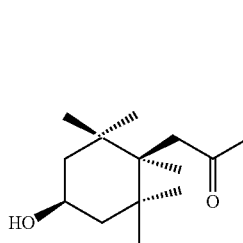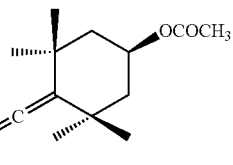

The most commonly described algae in terms of their fucoxanthin content are *Sargassum horneri, Hizikia fusiformis, Laminaria japonica* and *Undaria pinnatifida* [Kim and Pangestuti, "Biological activities and potential health benefits of fucoxanthin derived from marine brown algae", Advances in Food and Nutrition Research, (2011) Chapter 9, 64 pp 111-128]. In brown algae, fucoxanthin has an important biological function of protection against oxidative stress at the collecting antenna which enables photosynthesis [D. Siefermann-Harms, "*The light-harvesting and protective functions of carotenoids in photosynthetic membranes*" in: Physiologia Plantarum, (1987) Vol. 69(3) pp 561-568]. The synthesis of this molecule in algae is tightly regulated as a function of the light conditions [R. Goss, T. Jakob, "*Regulation and function of xanthophyll cycle-dependent photoprotection in algae*" in: Photosynthesis Research. (2010), Vol. 106(1-2) pp 103-122]. Fucoxanthin is, in the same way as reduced glutathione, α-tocopherol, β-carotene and the flavonoids, a response to overall oxidative stresses [N. Mallick, F. Mohn, "*Reactive oxygen species: response of algal cells*" in: J. Plant Physiology. (2000) Vol. 157 (2), pp 183-193]. Fucoxanthin has been widely described as having the following biological effects: antioxidant, anti-obesity, anti-cancer, anti-diabetic, anti-photoaging, protection of the cardiovascular system, anti-inflammatory, neuroprotection, anti-angiogenic, anti-tyrosinase (implying a depigmenting effect), or an osteoporosis-preventing effect [Kim and Pangestuti, "*Biological activities and potential health benefits of fucoxanthin derived from marine brown algae*", Advances in Food and Nutrition Research, (2011) Chapter 9, 64 pp 111-128; D'Orazio et al., "*Fucoxanthin: a treasure from the sea*" in: Marine Drugs, (2012), 10, pp 604-616.].

Due to these benefits for health and the skin, fucoxanthin, or extracts containing fucoxanthin, is/are widely used in various fields such as nutrition, cosmetics or pharmaceuticals.

The French patent application published under the number 2 837 383 discloses that extracts of *Undaria pinnatifida* had positive effects in vitro regarding attacks to which the skin is subjected (reactive oxygen species, heavy metals, carbon dioxide, cigarette smoke, chemical pollution, etc.); said algal extracts being aqueous extracts obtained from thalli or any part of thalli in fresh, frozen, dried, whole, fragmented or ground form. However, such aqueous extracts give rise to an effect which is not sufficiently satisfactory for a high-performance application in cosmetics or pharmaceuticals.

The French patent application published under the number 2 880 803 discloses the use of brown algae to obtain an anti-aging effect. However, the extract used in this patent application gives rise to an effect which is not sufficiently satisfactory for a potential application in cosmetics or pharmaceuticals. Moreover, this extract can only be incorporated into cosmetic formulations such as creams with difficulty.

This is why the inventors have endeavored to develop a novel brown alga extract having an improved anti-aging effect and which can be readily incorporated into cosmetic formulations which are in the form of creams.

According to a first aspect, a subject of the invention is a lipophilic extract of brown alga gametophytes, obtained by the process comprising the following successive steps:

a step A) of preparing an aqueous-alcoholic suspension of gametophyte cells by mixing an aqueous suspension of brown alga gametophyte cells with at least one aliphatic alcohol comprising from one to four carbon atoms;

a step B) of mixing said aqueous-alcoholic suspension of alga gametophyte cells obtained in step A) with at least one fatty acid triglyceride which comprises from eight to twenty-two carbon atoms;

a step C) of adding water to the multiphase mixture obtained in step B);

a step D) of isolating said lipophilic extract of brown alga gametophytes from the mixture obtained in step C).

In the definition of the lipophilic extract of brown alga gametophytes which is a subject of the present invention, the aqueous suspension of brown alga gametophyte cells used in step A of the process for obtaining same may be prepared as follows:

According to a step a), blades of mature sporophytes ready to sporulate are recovered from the brown alga used. Mature sporophytes are sporophytes comprising fertile zones.

According to a step b), the mature sporophytes recovered in step a) are arranged in tanks containing seawater and release their spores into the medium. The spores thus released begin their germination to give rise to gametophyte cells.

According to a step c), the gametophytes formed during step b) are isolated then placed in a container containing seawater containing at least one source of nitrogen such as sodium nitrate ($NaNO_3$) at a concentration of between 50 and 250 mg/l with a preference for 150 mg/l and a source of phosphorus such as sodium dihydrogen phosphate ($NaH_2PO_4$) at a concentration of between 5 and 75 mg/l with a preference for 50 mg/l. According to a particular mode of this step c), the aqueous suspension thus formed also has other mineral elements added to it, by addition of a nutrient medium such as Provasoli medium with the following composition:

| Provasoli medium | |
|---|---|
| $NaNO_3$ | 350 mg |
| Sodium glycerophosphate | 50 mg |
| $Fe(NH_4)_2(SO_4)_2, 6H_2O$ | 18 mg |

-continued

| Provasoli medium | |
|---|---|
| Na₂ EDTA | 15 mg |
| H₃BO₃ | 28.5 mg |
| FeCl₃, 6H₂O | 1.225 mg |
| MnSO₄, H₂O | 4.1 mg |
| ZnSO₄, 7H₂O | 0.55 mg |
| CoSO₄, 7H₂O | 0.12 mg |
| Vitamin B12 | 10 µg |
| Thiamine | 0.5 mg |
| Biotin | 5 µg |
| Tris buffer | 500 mg |
| Distilled water | 100 ml |

According to a step d), the gametophytes are cultivated in translucent culture tanks under bubbling of air, optionally with carbon dioxide added to it, at ambient temperature and under constant illumination. After 14 days of culture, the cells have multiplied and the amount of biomass is high. It is then suitable to recover the gametophyte cells present in culture by filtering the contents of the tank over a filtering sieve with a cut-off threshold of 80 µm, which retains the gametophytes at its surface. The brown alga gametophytes obtained are then rinsed in seawater.

According to a step e), the recovered gametophytes thus rinsed are placed in aqueous suspension. This aqueous suspension is then used in step A) of the process for obtaining said lipophilic extract of brown alga gametophytes.

During step A) of the process for obtaining said lipophilic extract of brown alga gametophytes as defined above, the aqueous suspension of gametophyte cells is mixed with the alcohol or the mixture of alcohols at a temperature of 20° C. for at least one hour at an amount of 5 to 30 liters of alcohol per kilogram of biomass, and more particularly at an amount of approximately 10 liters of alcohol per kilogram of biomass. Said at least one aliphatic alcohol comprising from one to four carbon atoms, used in step A) of the process for obtaining said lipophilic extract of brown alga gametophytes as defined above is more particularly chosen from ethanol, propanol, isopropanol, butanol, isobutanol, or a mixture of these alcohols; it is most particularly ethanol.

During step B) of the process for obtaining said lipophilic extract of brown alga gametophytes as defined above, said aqueous-alcoholic suspension of brown alga gametophyte cells obtained in step A) is mixed with at least one fatty acid triglyceride which comprises from eight to twenty-two carbon atoms. Said at least one fatty acid triglyceride comprising from eight to twenty-two carbon atoms is more particularly a mixture of fatty acid triglycerides which comprise from eight to ten carbon atoms. According to this step B), the mixture is stirred for at least one hour.

According to another particular aspect, said aqueous-alcoholic suspension of brown alga gametophyte cells obtained in step A) is mixed with said at least one fatty acid triglyceride which comprises from eight to twenty-two carbon atoms such that the weight ratio of the weight of brown alga gametophyte cells to the weight of fatty acid triglycerides which comprise from eight to twenty-two carbon atoms is greater than or equal to 2% and less than or equal to 10%, and more particularly greater than or equal to 5%. According to a most particular aspect, this weight ratio is approximately equal to 6%.

During step C) of the process for obtaining said lipophilic extract of brown alga gametophytes as defined above, the multiphase mixture obtained in step B) has water added to it at a temperature of 20° C. with stirring.

According to another particular aspect, said multiphase mixture obtained in step B) has water added to it such that the weight ratio of the weight of brown alga gametophyte cells to the weight of water is greater than or equal to 0.5% and less than or equal to 2%. According to a most particular aspect, this weight ratio is approximately equal to 1%.

Step D) of isolating said lipophilic extract of brown alga gametophytes from the mixture obtained in step C) is generally carried out in the following way: the mixture thus formed is filtered to remove the biomass. The filtrate is then separated by centrifugation to obtain the lipophilic extract of interest.

"Brown alga" denotes, in the lipophilic extract which is a subject of the present invention, the elements of the group consisting of the brown algae of the orders Ascoseirales, Asterocladales, Desmarestiales, Dictyotales, Dictyotophycidae, Discosporangiales, Discosporangiophycidae, Ectocarpales, Fucales, Fucophycidae, Ishigeales, Ishigeophycidae, Laminariales, Nemodermatales, Onslowiales, Phaeophyceae ordo incertae sedis, Phaeosiphoniellales, Ralfsiales, Scytothamnales, Sphacelariales, Sporochnales, Syringodermatales, and Tilopteridales, and more particularly the elements of the group consisting of the brown algae of the orders Laminariales, Fucales, Desmarestiales, Ectocarpales and Tilopteridales, and even more particularly the brown algae of the order Laminariales.

In the lipophilic extract which is a subject of the present invention, "brown alga" more particularly denotes the brown algae of the order Laminariales chosen from the brown algae of the family Alariaceae and of the family Laminariaceae.

In the lipophilic extract which is a subject of the present invention, "brown alga" more particularly denotes the brown algae of the order Laminariales of the family Laminariaceae, chosen from the group consisting of *Laminaria digitata*, *Laminaria saccharina*, *Laminaria hyperborea* and *Laminaria ochroleuca*.

In the lipophilic extract which is a subject of the present invention, "brown alga" more particularly denotes the brown alga of the order Laminariales and of the family Alariaceae which is the brown alga *Undaria pinnatifida*.

Optionally, after the rinsing, the gametophytes obtained in step d) for preparing the aqueous suspension of brown alga gametophyte cells used in step A) of the process for obtaining said lipophilic extract of brown alga gametophytes as defined above are lyophilized, generally in a tray freeze dryer, then ground to obtain a lyophilizate powder of brown alga gametophytes. This is why, according to another particular aspect, the process for obtaining said lipophilic extract of brown alga gametophytes as defined above also comprises:

a step $A_0$) of preparing said aqueous suspension of brown alga gametophyte cells used in step A) by rehydrating a lyophilizate powder of brown alga gametophyte cells.

The step $A_0$ as defined above is generally carried out immediately after the grinding of the lyophilized cells by mixing the powder with water so as to obtain a biomass containing especially from 5% to 50% by weight of solids, more particularly from 15% to 45% by weight of solids and most particularly approximately 35% of solids.

The lipophilic extract of brown algae cells obtained at the end of step D) of the process for obtaining said lipophilic extract of brown alga gametophytes as defined above may also contain water; it is then necessary to dry this solution by adding a desiccant salt, for example anhydrous sodium sulfate (NaSO$_4$). The dry lipophilic extract of brown algae cells is then filtered over a paper filter made of cellulose material. This is why, according to another particular aspect, the process for obtaining said lipophilic extract of brown alga gametophytes as defined above also comprises:
- a step E) of drying said lipophilic extract of brown alga gametophytes obtained in step D).

According to another more particular aspect, the extract as defined above is characterized in that the brown alga gametophyte cells used in the obtaining process originate from brown algae of the order Laminariales, chosen from the brown algae of the family Alariaceae and of the family Laminariaceae, more particularly originate from brown algae originating from the group consisting of *Laminaria digitata, Laminaria saccharina, Laminaria hyperborea, Laminaria ochroleuca* and *Undaria pinnatifida*.

According to another more particular aspect, the extract as defined above is characterized in that the brown alga gametophyte cells used in the obtaining process originate from the alga *Undaria pinnatifida*.

Another subject of the invention is the process for obtaining the lipophilic extract of brown alga gametophytes as defined above, comprising the following successive steps:
- a step A) of preparing an aqueous-alcoholic suspension of gametophyte cells by mixing an aqueous suspension of brown alga gametophyte cells with at least one aliphatic alcohol comprising from one to four carbon atoms;
- a step B) of mixing said aqueous-alcoholic suspension of alga gametophyte cells obtained in step A) with at least one fatty acid triglyceride which comprises from eight to twenty-two carbon atoms;
- a step C) of adding water to the multiphase mixture obtained in step B);
- a step D) of isolating said lipophilic extract of brown alga gametophytes from the mixture obtained in step C).

According to more particular modes of the process as defined above, it also comprises one or the other or both of the following steps:
- a step E) of drying said lipophilic extract of brown alga gametophytes obtained in step D);
- a step A$_0$) of preparing said aqueous suspension of brown alga gametophyte cells used in step A) by rehydrating a lyophilizate of brown alga gametophyte cells.

According to other particular modes of the process as defined above:
- During step A), said at least one aliphatic alcohol comprising from one to four carbon atoms is chosen from ethanol, propanol, isopropanol, butanol, isobutanol, or a mixture of these alcohols; it is most particularly ethanol; and/or:
- During step B), said at least one fatty acid triglyceride comprising from eight to twenty-two carbon atoms is a mixture of fatty acid triglycerides which comprise from eight to ten carbon atoms; and/or:
- During step B), the weight ratio of the weight of brown alga gametophyte cells to the weight of fatty acid triglycerides which comprise from eight to twenty-two carbon atoms is greater than or equal to 2% and less than or equal to 10%; and it is more particularly greater than or equal to 5%; and/or:
- The brown alga gametophyte cells used originate from brown algae of the order Laminariales, chosen from brown algae of the family Alariaceae and of the family Laminariaceae, more particularly originate from brown algae originating from the group consisting of *Laminaria digitata, Laminaria saccharina, Laminaria hyperborea, Laminaria ochroleuca* and *Undaria pinnatifida*, and more particularly originating from the alga *Undaria pinnatifida*.

Another subject of the invention is the use of the lipophilic extract of brown alga gametophytes as defined above with the aim of preventing or slowing the appearance of the signs of aging of the human skin or lips or else of eliminating said signs, said use being in a cosmetic composition, and also a process with the aim of preventing or slowing the appearance of the signs of aging of the human skin or lips or else of eliminating said signs, comprising at least one step of application, to the human skin or to the lips, of a cosmetic composition (C1) for topical use, comprising at least one cosmetically acceptable excipient and an effective amount of the lipophilic extract of brown alga gametophytes as defined above.

Another subject of the invention is the composition (C1) as defined above.

In the process as defined above, said composition (C1) is generally spread onto the surface of the skin to be treated, then the skin is massaged for a moment.

The expression "for topical use" used in the definition of the composition (C1) which is a subject of the present invention means that said composition (C1) is used by application to the skin, whether this is direct application or indirect application when said composition (C1) according to the invention is impregnated onto a support intended to be brought into contact with the skin (paper, wipe, textile, transdermal device, etc.).

The expression "cosmetically acceptable" used in the definition of the composition (C1) which is a subject of the present invention means, according to the directive of the Council of the European Economic Community, no. 76/768/EEC of 27 Jul. 1976, amended by the directive no. 93/35/EEC of 14 Jun. 1993, that it comprises any substance or preparation intended to be brought into contact with the various parts of the human body (epidermis, body hair and head hair system, nails, lips and genitals) or with the teeth and the oral mucosae, with a view, exclusively and predominantly, to cleaning them, fragrancing them, modifying the appearance thereof and/or correcting the bodily odor thereof and/or protecting them and/or maintaining the good state thereof.

"Effective amount" of the lipophilic extract of brown alga gametophytes as defined above is intended to mean, per 100% of the weight of said composition (C1), an amount of between 0.1% and 5% by weight, more particularly between 0.1% and 3% by weight, and even more particularly between 0.5% and 2% by weight of said lipophilic extract of brown alga gametophytes.

The composition (C1) which is a subject of the present invention is generally in the form of an aqueous or aqueous-alcoholic or aqueous-glycolic solution, in the form of a suspension, of an emulsion, of a microemulsion or of a nanoemulsion, whether of water-in-oil, oil-in-water, water-in-oil-in-water or oil-in-water-in-oil type, or in the form of a powder.

The composition (C1) which is a subject of the present invention may be packaged in a bottle, in a pump-type "bottle" device, in pressurized form in an aerosol device, in a device provided with an openwork wall, such as a grille, or in a device provided with a ball applicator ("roll-on").

Generally, the lipophilic extract of brown alga gametophytes which is a subject of the present invention is combined with chemical additives customarily used in the field of formulations for topical use, such as foaming and/or detergent surfactants, thickening and/or gelling surfactants, thickeners and/or gelling agents, stabilizers, film-forming compounds, solvents and cosolvents, hydrotropic agents, spring or mineral waters, plasticizers, emulsifiers and coemulsifiers, opacifiers, nacreous agents, overfatting agents, sequestering agents, chelating agents, oils, waxes, antioxidants, fragrances, essential oils, preservatives, conditioning agents, deodorants, whitening agents intended for bleaching body hair and the skin, active agents intended to provide a treating and/or protective action with respect to the skin or the hair, sunscreens, mineral fillers or pigments, particles which provide a visual effect or which are intended for encapsulating active agents, exfoliant particles, texturing agents, optical brighteners, and insect repellants.

As examples of foaming and/or detergent surfactants which may be combined with the lipophilic extract of brown alga gametophytes in the composition (C1), mention may be made of anionic, cationic, amphoteric or nonionic foaming and/or detergent surfactants.

Among the anionic foaming and/or detergent surfactants, mention may be made of alkali metal salts, alkaline earth metal salts, ammonium salts, amine salts or amino alcohol salts of alkyl ether sulfates, alkyl sulfates, alkylamido ether sulfates, alkylarylpolyether sulfates, monoglyceride sulfates, alpha-olefin sulfonates, paraffin sulfonates, alkyl phosphates, alkyl ether phosphates, alkyl sulfonates, alkylamide sulfonates, alkylaryl sulfonates, alkyl carboxylates, alkyl sulfosuccinates, alkyl ether sulfosuccinates, alkylamide sulfosuccinates, alkyl sulfoacetates, alkylsarcosinates, acylisethionates, N-acyltaurates, acyl lactylates, N-acylated derivatives of amino acids, N-acylated derivatives of peptides, N-acylated derivatives of proteins, or N-acylated derivatives of fatty acids.

Among the amphoteric foaming and/or detergent surfactants, mention may be made of alkyl betaines, alkylamido betaines, sultaines, alkylamidoalkyl sulfobetaines, imidazoline derivatives, phosphobetaines, amphopolyacetates and amphopropionates.

Among the cationic foaming and/or detergent surfactants, mention may particularly be made of quaternary ammonium derivatives.

Among the nonionic foaming and/or detergent surfactants, mention may more particularly be made of alkyl polyglycosides comprising a linear or branched, saturated or unsaturated aliphatic radical, comprising from 8 to 16 carbon atoms, such as octylpolyglucoside, decylpolyglucoside, undecylenylpolyglucoside, dodecylpolyglucoside, tetradecylpolyglucoside, hexadecylpolyglucoside, 1,12-dodecanediylpolyglucoside; ethoxylated derivatives of hydrogenated castor oil, such as the product sold under the INCI name "Peg-40 hydrogenated castor oil"; polysorbates such as Polysorbate 20, Polysorbate 40, Polysorbate 60, Polysorbate 70, Polysorbate 80 or Polysorbate 85; coconut amides; N-alkylamines.

As examples of thickening and/or gelling surfactants which may be combined with the lipophilic extract of brown alga gametophytes in the composition (C1), mention may be made of optionally alkoxylated alkyl polyglucoside fatty esters, such as ethoxylated methylpolyglucoside esters such as PEG 120 methyl glucose trioleate and PEG 120 methyl glucose dioleate sold respectively under the names Glucamate™ LT and Glumate™ DOE120; alkoxylated fatty esters such as PEG 150 pentaerythrytyl tetrastearate sold under the name Crothix™ DS53, PEG 55 propylene glycol oleate sold under the name Antil™ 141; fatty-chain polyalkylene glycol carbamates, such as PPG-14 laureth isophoryl dicarbamate sold under the name Elfacos™ T211, or PPG-14 palmeth-60 hexyl dicarbamate sold under the name Elfacos™ GT2125.

As examples of thickeners and/or gelling agents which may be combined with the lipophilic extract of brown alga gametophytes in the composition (C1), mention may be made of linear or branched or crosslinked polymers of polyelectrolyte type, such as partially or totally salified acrylic acid homopolymer, partially or totally salified methacrylic acid homopolymer, partially or totally salified 2-methyl-[(1-oxo-2-propenyl)amino]-1-propane sulfonic acid (AMPS) homopolymer, copolymers of acrylic acid and of AMPS, copolymers of acrylamide and of AMPS, copolymers of vinylpyrolidone and of AMPS, copolymers of AMPS and of (2-hydroxyethyl) acrylate, copolymers of AMPS and of (2-hydroxyethyl) methacrylate, copolymers of AMPS and of hydroxyethylacrylamide, copolymers of AMPS and of N,N-dimethylacrylamide, copolymers of AMPS and of tris(hydroxy-methyl)acrylamidomethane (THAM), copolymers of acrylic or methacrylic acid and of (2-hydroxyethyl) acrylate, copolymers of acrylic or methacrylic acid and of (2-hydroxyethyl) methacrylate, copolymers of acrylic or methacrylic acid and of hydroxyethylacrylamide, copolymers of acrylic or methacrylic acid and of THAM, copolymers of acrylic or methacrylic acid and of N,N-dimethylacrylamide, terpolymers of acrylic or methacrylic acid, of AMPS and of (2-hydroxyethyl) acrylate, terpolymers of acrylic or methacrylic acid, of AMPS and of (2-hydroxyethyl) methacrylate, terpolymers of acrylic or methacrylic acid, of AMPS and of THAN, terpolymers of acrylic or methacrylic acid, of AMPS and of N,N dimethylacrylamide, terpolymers of acrylic or methacrylic acid, of AMPS and of acrylamide, copolymers of acrylic acid or methacrylic acid and of alkyl acrylates of which the carbon-based chain comprises between four and thirty carbon atoms, and more particularly between ten and thirty carbon atoms, copolymers of AMPS and of alkyl acrylates of which the carbon-based chain comprises between four and thirty carbon atoms and more particularly between ten and thirty carbon atoms, linear, branched or crosslinked terpolymers of at least one monomer having a free, partially salified or totally salified strong acid function, with at least one neutral monomer and at least one monomer of formula (VIII):

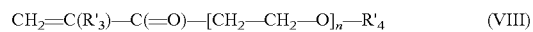

$$CH_2=C(R'_3)-C(=O)-[CH_2-CH_2-O]_n-R'_4 \quad (VIII)$$

in which $R'_3$ represents a hydrogen atom or a methyl radical, $R'_4$ represents a linear or branched alkyl radical comprising from eight to thirty carbon atoms, and n represents a number greater than or equal to one and less than or equal to fifty.

The linear or branched or crosslinked polymers of polyelectrolyte type which may be combined with the lipophilic extract of brown alga gametophytes in the composition (C1) may be in the form of a solution, an aqueous suspension, a water-in-oil emulsion, an oil-in-water emulsion, or a powder. The linear or branched or crosslinked polymers of polyelectrolyte type which may be combined with the lipophilic extract of brown alga gametophytes in the composition (C1) may be selected from the products sold under the names Simulgel™ EG, Simulgel™ EPG, Sepigel™ 305, Simulgel™ 600, Simulgel™ NS, Simulgel™ INS 100, Simulgel™ FL, Simulgel™ A, Simulgel™ SMS 88, Sepinov™EMT 10, Sepiplus™400, Sepiplus™265, Sepiplus™S, Sepimax™ZEN, Aristoflex™AVC, Aristoflex™AVS, Novemer™EC-1, Novemer™EC-2, Aristoflex™HMB, Cosmedia™SP, Flocare™ET 25, Flocare™ET 75, Flocare™ET 26, Flocare™ET 30, Flocare™ET 58, Flocare™PSD 30, Viscolam™AT 64, Viscolam™AT 100.

As examples of thickeners and/or gelling agents which may be combined with the lipophilic extract of brown alga gametophytes in the composition (C1), mention may be made of polysaccharides consisting only of monosaccharides, such as glucans or glucose homopolymers, glucomannoglucans, xyloglycans, galactomannans of which the degree of substitution (DS) of the D-galactose units on the main chain of D-mannose is between 0 and 1, and more particularly between 1 and 0.25, such as galactomannans originating from cassia gum (DS=⅕), from locust bean gum (DS=¼), from tara gum (DS=⅓), from guar gum (DS=½) or from fenugreek gum (DS=1).

As examples of thickeners and/or gelling agents which may be combined with the lipophilic extract of brown alga gametophytes in the composition (C1), mention may be made of polysaccharides consisting of monosaccharide derivatives, such as sulfated galactans and more particularly carrageenans and agar, uronans and more particularly algins, alginates and pectins, heteropolymers of monosaccharides and of uronic acids and more particularly xanthan gum, gellan gum, exudates of gum Arabic and of karaya gum, and glucosaminoglycans.

As examples of thickeners and/or gelling agents which may be combined with the lipophilic extract of brown alga gametophytes in the composition (C1), mention may be made of cellulose, cellulose derivatives, such as methylcellulose, ethylcellulose, hydroxypropylcellulose, silicates, starch, hydrophilic starch derivatives, and polyurethanes.

As examples of stabilizers which may be combined with the lipophilic extract of brown alga gametophytes in the composition (C1), mention may for example be made of microcrystalline waxes, and more particularly ozokerite, mineral salts such as sodium chloride or magnesium chloride, and silicone polymers such as polysiloxane polyalkyl polyether copolymers.

As examples of solvents which may be combined with the lipophilic extract of brown alga gametophytes in the composition (C1), mention may be made of water, organic solvents, such as glycerol, diglycerol, glycerol oligomers, ethylene glycol, propylene glycol, butylene glycol, 1,3-propanediol, 1,2-propanediol, hexylene glycol, diethylene glycol, xylitol, erythritol, sorbitol, water-soluble alcohols such as ethanol, isopropanol or butanol, and mixtures of water and of said organic solvents.

As examples of spring or mineral waters which may be combined with the lipophilic extract of brown alga gametophytes in the composition (C1), mention may be made of spring or mineral waters having a mineralization of at least 300 mg/l, in particular Avine water, Vittel water, waters from the Vichy basin, Uriage water, la Roche Posay water, la Bourboule water, Enghien-les-bains water, Saint-Gervais-les-bains water, Néris-les-bains water, Allevard-les-bains water, Digne water, Maizières water, Neyrac-les-bains water, Lons le Saunier water, Rochefort water, Saint Christau water, Fumades water and Tercis-les-bains water.

As examples of hydrotropic agents which may be combined with the lipophilic extract of brown alga gametophytes in the composition (C1), mention may be made of the xylene sulfonates, cumene sulfonates, hexylpolyglucoside, 2-ethylhexylpolyglucoside and n-heptylpolyglucoside.

As examples of emulsifying surfactants which may be combined with the lipophilic extract of brown alga gametophytes in the composition (C1), mention may be made of nonionic surfactants, anionic surfactants and cationic surfactants.

As examples of nonionic emulsifying surfactants which may be combined with the lipophilic extract of brown alga gametophytes in the composition (C1), mention may be made of fatty acid esters of sorbitol, such as the products sold under the names Montane™40, Montane™60, Montane™70, Montane™80 and Montane™85; compositions comprising glyceryl stearate and stearic acid ethoxylated at between 5 mol and 150 mol of ethylene oxide, such as the composition comprising stearic acid ethoxylated at 135 mol of ethylene oxide and glyceryl stearate sold under the name Simulsol™ 165; mannitan esters; ethoxylated mannitan esters; sucrose esters; methylglucoside esters; alkyl polyglycosides comprising a linear or branched, saturated or unsaturated aliphatic radical, comprising from fourteen to thirty-six carbon atoms, such as tetradecylpolyglucoside, hexadecylpolyglucoside, octadecylpolyglucoside, hexadecylpolyxyloside, octadecylpolyxyloside, eicosylpolyglucoside, dodecosylpolyglucoside, 2-octyldodecylpolyxyloside or 12-hydroxystearylpolyglucoside; compositions of linear or branched, saturated or unsaturated fatty alcohols, comprising from fourteen to thirty-six carbon atoms, and of alkyl polyglycosides as described above, for example the compositions sold under the trade names Montanov™68, Montanov™14, Montanov™82, Montanov™202, Montanov™S, Montanov™WO18, Montanov™L, Fluidanov™20X and Easynov™.

As examples of anionic surfactants which may be combined with the lipophilic extract of brown alga gametophytes in the composition (C1), mention may be made of glyceryl stearate citrate, cetearyl sulfate, soaps, such as sodium stearate or triethanolammonium stearate, and N-acylated derivatives of amino acids which are salified, for example stearoyl glutamate.

As examples of cationic emulsifying surfactants which may be combined with the lipophilic extract of brown alga gametophytes in the composition (C1), mention may be made of amine oxides, quaternium-82 and the surfactants described in the patent application published under number WO 96/00719 and mainly those in which the fatty chain comprises at least sixteen carbon atoms.

As examples of opacifiers and/or nacreous agents which may be combined with the lipophilic extract of brown alga gametophytes in the composition (C1), mention may be made of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate, and fatty alcohols comprising from twelve to twenty-two carbon atoms.

As examples of texturing agents which may be combined with the lipophilic extract of brown alga gametophytes in the composition (C1), mention may be made of N-acylated derivatives of amino acids, for example the lauroyl lysine sold under the name Aminohope™LL, the octenyl starch succinate sold under the name Dryflo™, the myristyl polyglucoside sold under the name Montanov™ 14, cellulose fibers, cotton fibers, chitosan fibers, talc, sericite and mica.

As examples of deodorants which may be combined with the lipophilic extract of brown alga gametophytes in the composition (C1), mention may be made of alkali metal silicates, zinc salts such as zinc sulfate, zinc gluconate, zinc chloride or zinc lactate; quaternary ammonium salts such as cetyltrimethylammonium salts, cetylpyridinium salts; glycerol derivatives such as glyceryl caprate, glyceryl caprylate, polyglyceryl caprate; 1,2-decanediol; 1,3-propanediol; salicylic acid; sodium bicarbonate; cyclodextrins; metal zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octochlorohydrate, aluminum sulfate, sodium aluminum lactate, complexes of aluminum chlorohydrate and glycol, such as the complex of aluminum chlorohydrate and of propylene glycol, the complex of aluminum dichlorohydrate and of propylene glycol, the complex of aluminum sesquichlorohydrate and of propylene glycol, the complex of aluminum chlorohydrate and of polyethylene glycol, the complex of aluminum dichlorohydrate and of polyethylene glycol, and the complex of aluminum sesquichlorohydrate and of polyethylene glycol.

As examples of oils which may be combined with the lipophilic extract of brown alga gametophytes in the composition (C1), mention may be made of mineral oils such as paraffin oil, liquid petroleum jelly, isoparaffins or white mineral oils; oils of animal origin, such as squalene or squalane; vegetable oils, such as phytosqualane, sweet almond oil, coconut oil, castor oil, jojoba oil, olive oil, rapeseed oil, peanut oil, sunflower oil, wheatgerm oil, corn germ oil, soybean oil, cottonseed oil, alfalfa oil, poppyseed oil, pumpkin oil, evening primrose oil, millet oil, barley oil, rye oil, safflower oil, candle nut oil, passion flower oil, hazelnut oil, palm oil, shea butter, apricot kernel oil, betel leaf oil, sysymbrium oil, avocado oil, calendula oil, oils derived from flowers or from vegetables, ethoxylated vegetable oils; synthetic oils, such as fatty acid esters such as butyl myristate, propyl myristate, isopropyl myristate, cetyl myristate, isopropyl palmitate, octyl palmitate, butyl stearate, hexadecyl stearate, isopropyl stearate, octyl stearate, isocetyl stearate, dodecyl oleate, hexyl laurate, propylene glycol dicaprylate, lanolic acid-derived esters, such as isopropyl lanolate, isocetyl lanolate, fatty acid monoglycerides, diglycerides and triglycerides, such as glyceryl triheptanoate, alkyl benzoates, hydrogenated oils, poly(alpha-olefin)s, polyolefins, such as poly(isobutane), synthetic isoalkanes, such as isohexadecane, isododecane, perfluoro oils; silicone oils, such as dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups. The term "oils" is intended to mean, in the present application, compounds and/or mixtures of compounds which are insoluble in water and which have a liquid appearance at a temperature of 25° C.

As examples of waxes which may be combined with the lipophilic extract of brown alga gametophytes in the composition (C1), mention may be made of beeswax, carnauba wax, candelilla wax, ouricury wax, Japan wax, cork fiber wax, sugarcane wax, paraffin waxes, lignite waxes, microcrystalline waxes, lanolin wax; ozokerite; polyethylene wax; silicone waxes; vegetable waxes; fatty alcohols and fatty acids which are solid at ambient temperature; glycerides which are solid at ambient temperature. The term "waxes" is intended to mean, in the present application, compounds and/or mixtures of compounds which are insoluble in water and which have a solid appearance at a temperature greater than or equal to 45° C.

As examples of active agents which may be combined with the lipophilic extract of brown alga gametophytes in the composition (C1), mention may be made of vitamins and derivatives thereof, especially esters thereof, such as retinol (vitamin A) and esters thereof (retinyl palmitate for example), ascorbic acid (vitamin C) and esters thereof, sugar derivatives of ascorbic acid (such as ascorbyl glucoside), tocopherol (vitamin E) and esters thereof (such as tocopheryl acetate), vitamin B3 or B10 (niacinamide and derivatives thereof); compounds showing a skin-lightening or skin-depigmenting action, such as the ω-undecylenoyl phenylalanine sold under the name Sepiwhite™MSH, Sepicalm™VG, the glycerol monoester and/or diester of ω-undecelynoyl phenylalanine, ω-undecylenoyl dipeptides, arbutin, kojic acid, hydroquinone; compounds showing a soothing action, in particular Sepicalm™ S, allantoin and bisabolol; anti-inflammatories; compounds showing a moisturizing action, such as urea, hydroxyureas, glycerol, polyglycerols, glycerolglucoside, diglycerolglucoside, polyglycerylglucosides, xylitylglucoside, the composition sold under the trade name Aquaxyl™, the composition sold under the trade name Pro-Xylane™, C-glycoside derivatives and more particularly C-glucoside or C-xyloside derivatives; polyphenol-rich plant extracts, such as grape extracts, pine extracts, wine extracts, olive extracts; compounds showing a slimming or lipolytic action, such as caffeine or derivatives thereof, Adiposlim™, Adipoless™, fucoxanthin; N-acylated proteins; N-acylated peptides, such as Matrixil™; N-acylated amino acids; partial hydrolysates of N-acylated proteins; amino acids; peptides; total protein hydrolysates; soybean extracts, for example Raffermine™; wheat extracts, for example Tensine™ or Gliadine™; plant extracts, such as tannin-rich plant extracts, isoflavone-rich plant extracts or terpene-rich plant extracts; extracts of freshwater or seawater algae; marine plant extracts; marine extracts in general, such as corals; essential waxes; bacterial extracts; ceramides; phospholipids; compounds showing an antimicrobial action or a purifying action, such as Lipacide™ C8G, Lipacide™ UG, Sepicontrol™ A5, Fluidipure™8G; Octopirox™ or Sensiva™ SC50; compounds showing an energizing or stimulating property, such as Physiogenyl™, panthenol and derivatives thereof, such as Sepicap™ MP; anti-aging active agents, such as Sepilift™ DPHP, Lipacide™ PVB, Sepivinol™, Sepivital™, Manoliva™, Phyto-Age™, Timecode™; Survicode™; anti-photoaging active agents; active agents for protecting the integrity of the dermoepidermal junction; active agents for increasing the synthesis of extracellular matrix components such as collagen, elastins, glycosaminoglycans; active agents which act favorably on chemical cell communication, such as cytokines, or physical cell communication, such as integrins; active agents which create a "heating" sensation on the skin, such as skin microcirculation activators (such as nicotinic acid derivatives) or products which create a feeling of "coolness" on the skin (such as menthol and derivatives); active agents for improving skin microcirculation, for example veinotonics; draining active agents; active agents for decongestive purposes, such as extracts of *ginko biloba*, of ivy, of horse chestnut, of bamboo, of ruscus, of butcher's broom, of *Centalla asiatica*, of fucus, of rosemary, of willow; agents for tanning or browning the skin, such as dihydroxyacetone (DHA), erythrulose, mesotartric aldehyde, glutaraldehyde, glyceraldehyde, alloxane, ninhydrin, plant extracts, for example extracts of red woods of the *Pterocarpus* genus and of the *Baphia* genus, such as *Pterocarpus santalinus, Pterocarpus osun, Pterocarpus soyauxii, Pterocarpus erinaceus, Pterocarpus indicus* or else *Baphia nitida*, such as those described in European patent application EP 0 971 683; agents known for their action in facilitating and/or accelerating the tanning and/or browning of the human skin and/or for their action in coloring the human skin, for example the carotenoids (and more particularly beta-carotene and gamma-carotene), the product sold under the name "carrot oil" (INCI name: *Daucus Carota*, helianthis *annuus* sunflower oil) by Provital, which contains carotenoids, vitamin E and vitamin K; tyrosine and/or derivatives thereof, known for their effect in accelerating the tanning of the human skin in combination with exposure to ultraviolet radiation, for example the product sold under the trade name "Sun Tan Accelerator™" by Provital which contains tyrosine and riboflavins (vitamin B), the complex of tyrosine and tyrosinase sold under the trade name "Zymo Tan Complex" by Zymo Line, the product sold under the trade name MelanoBronze™ (INCI name: Acetyl Tyrosine, Monk's pepper extract (Vitex agnus-castus)) by Mibelle which contains acetyl tyrosine, the product sold under the trade name Unipertan VEG-24/242/2002 (INCI name: butylene glycol and Acetyl Tyrosine and hydrolyzed vegetable protein and Adenosine triphosphate) by UNIPEX, the product sold under the trade name "Try-Excell™" (INCI name: Oleoyl Tyrosine and Luffa *Cylindrica* (Seed) Oil and Oleic acid) by Sederma which contains extracts of marrow seeds (or Loofah oil), the product sold under the trade name "Actibronze™" (INCI name: hydrolyzed wheat protein and acetyl tyrosine and copper gluconate) by Alban Muller, the product sold under the trade name Tyrostan™ (INCI name: potassium caproyl tyrosine) by Synerga, the product sold under the trade name Tyrosinol (INCI name: Sorbitan Isostearate, glyceryl oleate, caproyl Tyrosine) by Synerga, the product sold under the trade name InstaBronze™ (INCI name: Dihydroxyacetone and acetyl tyrosine and copper gluconate) sold by Alban Muller, the product sold under the trade name Tyrosilane (INCI name: methylsilanol and acetyl tyrosine) by Exymol; peptides known for their effect of activation of melanogenesis, for example the product sold under the trade name Bronzing SF Peptide powder (INCI name: Dextran and Octapeptide-5) by Infinitec Activos, the product sold under the trade name Melitane (INCI name: Glycerin and Aqua and Dextran and Acetyl hexapeptide-1) comprising acetyl hexapeptide-1 known for its alpha-MSH agonist action, the product sold under the trade name Melatimes Solutions™ (INCI name: Butylene glycol, Palmitoyl Tripeptide-40) by LIPOTEC, sugars and sugar derivatives, for example the product sold under the trade name Tanositol™ (INCI name: inositol) by Provital, the product sold under the trade name Thalitan™ (or Phycosaccharide™ AG) by CODIF international (INCI name: Aqua and hydrolyzed algin (*Laminaria digitata*) and magnesium sulfate and manganese sulfate) containing an oligosaccharide of marine origin (guluronic acid and mannuronic acid chelated with magnesium and manganese ions), the product sold under the trade name Melactiva™ (INCI name: Maltodextrin, *Mucuna Pruriens* Seed extract) by Alban Muller, flavonoid-rich compounds, for example the product sold under the trade name "Biotanning" (INCI name: Hydrolyzed citrus *Aurantium dulcis* fruit extract) by Silab and known to be rich in lemon flavonoids (of hesperidin type); agents intended for treating head hair and/or body hair, for example agents which protect the melanocytes of the hair follicle, intended to protect said melanocytes against cytotoxic agents which are responsible for the senescence and/or apoptosis of said melanocytes, such as mimetics of dopachrome tautomerase activity, chosen from those described in the European patent application published under the number EP 1 515 688 A2, synthetic SOD mimetic molecules, for example manganese complexes, antioxidant compounds, for example cyclodextrin derivatives, siliceous compounds derived from ascorbic acid, lysine or arginine pyrrolidonecarboxylate, combinations of mono- and diesters of cinnamic acid and of vitamin C, and more generally those mentioned in the European patent application published under the number EP 1 515 688 A2.

As examples of antioxidants which may be combined with the lipophilic extract of brown alga gametophytes in the composition (C1), mention may be made of EDTA and the salts thereof, citric acid, tartaric acid, oxalic acid, BHA (butylhydroxyanisole), BHT (butylhydroxytoluene), tocopherol derivatives such as tocopherol acetate, mixtures of antioxidant compounds such as Dissolvine™ GL 47S, sold by Akzo Nobel under the INCI name: Tetrasodium Glutamate Diacetate.

As examples of sunscreens which may be combined with the lipophilic extract of brown alga gametophytes in the composition (C1), mention may be made of all those included in the amended cosmetics directive 76/768/EEC, annex VII.

Among the organic sunscreens which may be combined with the lipophilic extract of brown alga gametophytes in the composition (C1), mention may be made of the family of benzoic acid derivatives, such as para-aminobenzoic acids (PABAs), especially monoglyceryl esters of PABA, ethyl esters of N,N-propoxy PABA, ethyl esters of N,N-diethoxy PABA, ethyl esters of N,N-dimethyl-PABA, methyl esters of N,N-dimethyl-PABA, butyl esters of N,N-dimethyl-PABA; the family of anthranilic acid derivatives, such as homomenthyl-N-acetyl anthranilate; the family of salicylic acid derivatives, such as amyl salicylate, homomenthyl salicylate, ethylhexyl salicylate, phenyl salicylate, benzyl salicylate, or p-isopropanolphenyl salicylate; the family of cinnamic acid derivatives, such as ethylhexyl cinnamate, ethyl 4-isopropyl cinnamate, methyl 2,5-diisopropyl cinnamate, propyl p-methoxycinnamate, isopropyl p-methoxycinnamate, isoamyl p-methoxycinnamate, octyl p-methoxycinnamate, 2-ethylhexyl p-methoxycinnamate, 2-ethoxyethyl p-methoxycinnamate, cyclohexyl p-methoxycinnamate, ethyl α-cyano-β-phenylcinnamate, 2-ethylhexyl α-cyano-β-phenylcinnamate, mono(2-ethylhexanoyl)glyceryl di(para-methoxycinnamate); the family of benzophenone derivatives, such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octyloxybenzophenone, 4-hydroxy-3-carboxybenzophenone; 3-(4'-methylbenzylidene)-d,l-camphor, 3-(benzylidene)-d,l-camphor, camphor benzalkonium methosulfate; urocanic acid, ethyl urocanate; the family of sulfonic acid derivatives, such as 2-phenylbenzimidazole-5 sulfonic acid and salts thereof; the family of triazine derivatives, such as hydroxyphenyl triazine, ethylhexyloxyhydroxyphenyl-4-methoxyphenyltriazine, 2,4,6-trianillino-(p-carbo-2'-ethylhexyl-1'-oxy)-1,3,5-triazine, benzoic acid 4,4-((6-(((1,1-dimethylethyl)amino)carbonyl)phenyl)amino)-1,3,5-triazine-2,4-diyl diimino) bis(2-ethylhexyl) ester, 2-phenyl-5-methylbenzoxazole, 2,2'-hydroxy-5'-methylphenylbenzotriazole, 2-(2'-hydroxy-5'-t-octylphenyl)benzotriazole, 2-(2'-hydroxy-5'-methylphenyl) benzotriazole; dibenzazine; dianisoylmethane, 4-methoxy-4"-t-butylbenzoylmethane; 5-(3,3-dimethyl-2-norbornylidene)-3-pentan-2-one; the family of diphenyl acrylate derivatives, such as 2-ethylhexyl-2-cyano-3,3-diphenyl-2-propenoate, ethyl-2-cyano-3,3-diphenyl-2-propenoate; the family of polysiloxanes, such as benzylidene siloxane malonate.

Among the inorganic sunscreens, also known as "mineral screens", which may be combined with the lipophilic extract of brown alga gametophytes in the composition (C1), mention may be made of titanium oxides, zinc oxides, cerium oxide, zirconium oxide, yellow, red or black iron oxides, and chromium oxides. These mineral screens may or may not be micronized, may or may not have undergone surface treatments and may be optionally present in the form of aqueous or oil predispersions.

Another subject of the invention is the lipophilic extract of brown alga gametophytes as defined above, for the use thereof in a method for the therapeutic treatment of the signs of aging of the human skin or the lips, applied to the human body.

The following examples illustrate the invention, without, however, limiting it.

List of Extracts Tested

Extract A (according to the invention): extract of *Undaria pinnatifida* gametophytes.

Extract B (according to the prior art): extract BB of example 3 of French patent application FR 2 880 803 A1.

Extract C (according to the prior art): extract of *Undaria pinnatifida* sporophyte, obtained by extraction in a mixture of water and glycerol.

Biological Effectiveness of Extracts Tested

In Vitro Study

The model chosen to demonstrate the technical effect of the extract according to the invention is a model for studying the expression of genes on human skin explants. The tests, referred to as genomic or transcriptomic tests, are very widely used in various fields such as cosmetics, in order to demonstrate biological benefits. Working with human skin explants makes it possible to work under more physiological conditions than when working with monolayer cell cultures.

Human skin explants approximately 10 mm in diameter, originating from 2 female Caucasian donors (49 years and 46 years), resulting from abdominal surgical waste, were taken. They were then kept alive in a specific BEM medium (Bio-Ec's Explants Medium) at 37° C. in a humid atmosphere containing 5% $CO_2$. The products indicated in table 1 were then applied for a duration of 24 h.

TABLE 1

Means of application of the products.

| Extract | Physical appearance | Concentration applied topically | Concentration applied in the culture medium |
|---|---|---|---|
| A | Dark green liquid | 1% | 0.1% |
| B | Light green liquid | 1% | 0.1% |
| C | Colorless liquid | 1% | 0.1% |
| Carrier | Colorless liquid | 2.5% in aqueous gel | 1% |

The products were prepared in an aqueous-alcoholic gel containing 2.5% ethanol for topical applications, and with 1% ethanol in the culture medium in order to be dissolved. 3 explants per condition were thus prepared. After 24 h, the total RNAs were extracted and then quantitative and qualitative analysis was carried out in order to determine their concentration and their degree of purity and integrity before subjecting them to an amplification step. 50 ng of RNA were thus subsequently used, then reverse transcribed in order to obtain a complementary DNA. The latter was then amplified by qPCR (quantitative polymerase chain reaction) by means of probes specific to 3 genes: GAPDH (housekeeping gene, control), HIF-1a and SIRT-1, and of a fluorescent dye, SYBR green, making it possible to monitor the amplification reaction in real time. PCR runs in cycles, and the number of cycles (Cq) carried out for each target, in order for the latter to be detectable, is reported. This cycle value is then subtracted from that of GAPDH in order to standardize the effects obtained, then the expression ratio relative to the carrier condition is calculated (RQ).

For each extract tested, and for each gene of interest, the following values are calculated:

$$\Delta Cq \text{ (extract } i) = Cq \text{ (gene of interest)} - Cq \text{ (reference gene)}$$

with:

Cq (gene of interest) representing the mean number of cycles carried out and necessary to obtain a signal for a given extract and a given gene of interest;

Cq (reference gene) representing the mean number of cycles carried out and necessary to obtain a signal for a given extract and a reference gene (in this case GAPDH).

For each gene of interest and for each extract tested, the following calculation is performed:

$$\Delta\Delta Cq = \Delta Cq \text{ (extract } i) - \Delta Cq \text{ of the carrier}$$

For each extract tested, and for each gene of interest, the RQ value is calculated according to:

$$RQ = 2^{-\Delta\Delta Cq}$$

The variation results are presented in table 2 below.

TABLE 2

Results of gene expression obtained

| | GAPDH | | HIF-1a | | SIRT-1 | |
|---|---|---|---|---|---|---|
| | Mean number of cycles | Mean RQ | Mean number of cycles | Mean RQ | Mean number of cycles | Mean RQ |
| Extract | | | | | | |
| A | 20.21 | 1 | 24.99 | 1.41 | 28.27 | 1.56 |
| B | 19.85 | 1 | 24.88 | 0.6 | 28.28 | 0.73 |
| C | 19.99 | 1 | 24.94 | 0.67 | 28.10 | 0.82 |
| Carrier | | | | | | |
| (a) | 20.02 | | 25.38 | | 27.91 | |
| (b) | 21.12 | | 25.41 | | 28.83 | |

(a): experiment carried out with compound A
(b): experiment carried out with the other compounds The extract A (extract of *Undaria pinnatifida* gametophytes) makes it possible to induce overexpression of the genes HIF-1a and SIRT-1 compared to the carrier condition. The other compounds do not make it possible to induce the expression of these genes. The present results make it possible to demonstrate the additional technical effect of the invention over the closest prior art represented by the aqueous extract of *Undaria pinnatifida* sporophyte (extract C) and by the extract BB from the patent application FR 2 880 803 A1 (extract B).

In Vivo Study

A clinical trial, carried out on a representative panel of subjects (25 women), made it possible to demonstrate an effect of reducing the redness of the cutaneous micro-relief and the mean depth of wrinkles in the "crow's feet" region, associated with the application, to the region of the skin in question, of a cosmetic formulation comprising an effective amount of extract A according to the invention compared to the application, to the same region of the skin, of a "placebo" cosmetic formulation not comprising said extract A, for two months.

Another clinical trial, carried out on a representative panel of subjects (mixed panel comprising 20 people) made it possible to demonstrate an effect of improving the antioxidant ability of the skin associated with the application, to the skin, of a cosmetic formulation comprising an effective amount of extract A according to the invention compared to the application, to the skin, of a "placebo" cosmetic formulation not comprising said extract A, after 14 and 28 days of applications. This effect was demonstrated by using the ferric reducing ability test of antioxidant power (referred to as the FRAP method).

Another clinical assessment was carried out on this same representative panel of subjects and made it possible to demonstrate an effect of improving the resistance of the skin to a stress induced by exposure to ultraviolet A radiation associated with the application, to the skin, of a cosmetic formulation comprising an effective amount of extract A according to the invention compared to the application, to the skin, of a "placebo" cosmetic formulation not comprising said extract A, after 14 and 28 days of applications. This effect was demonstrated by using the malondialdehyde (MDA) assay method, MDA being the main product of lipid peroxidation, by the method of Erdelmeier et al., 1998, based on the ability of a chromogen, NMPI (N-methyl-2-phenylindole) to react with the MDA at 45° C. and at acid pH to produce a stable chromophore with an absorption peak at 586 nm.

The invention claimed is:

1. A process for obtaining a lipophilic extract of brown alga gametophytes, comprising the following successive steps:
   a step A) of preparing an aqueous-alcoholic suspension of gametophyte cells by mixing an aqueous suspension of brown alga gametophyte cells with at least one aliphatic alcohol comprising from one to four carbon atoms;
   a step B) of mixing said aqueous-alcoholic suspension of alga gametophyte cells obtained in step A) with at least one fatty acid triglyceride which comprises from eight to twenty-two carbon atoms;
   a step C) of adding water to the multiphase mixture obtained in step B);
   a step D) of isolating said lipophilic extract of brown alga gametophytes from the mixture obtained in step C).

2. The process as defined in claim 1, according to which, during step A), said at least one aliphatic alcohol comprising from one to four carbon atoms is chosen from ethanol, propanol, isopropanol, butanol, isobutanol or a mixture of these alcohols.

3. The process as defined in claim 2, according to which, during step A), said at least one aliphatic alcohol comprising from one to four carbon atoms is ethanol.

4. The process as defined in claim 1, according to which, during step B), said at least one fatty acid triglyceride comprising from eight to twenty-two carbon atoms is a mixture of fatty acid triglycerides which comprise from eight to ten carbon atoms.

5. The process as defined in claim 1, according to which, during step B), the weight ratio of the weight of brown alga gametophyte cells to the weight of fatty acid triglycerides which comprise from eight to twenty-two carbon atoms is greater than or equal to 2% and less than or equal to 10%.

6. The process as defined in claim 5, according to which, during step B), said weight ratio of the weight of brown alga gametophyte cells to the weight of fatty acid triglycerides which comprise from eight to twenty-two carbon atoms is greater than or equal to 5%.

7. The process as defined in claim 1, also comprising a step $A_0$) of preparing said aqueous suspension of brown alga gametophyte cells used in step A) by rehydrating a lyophilizate of brown alga gametophyte cells.

8. The process as defined in claim 1, also comprising:
   a step E) of drying said lipophilic extract of brown alga gametophytes obtained in step D).

9. The process as defined in claim 7, also comprising:
   a step E) of drying said lipophilic extract of brown alga gametophytes obtained in step D).

10. The process as defined in claim 1, in which the brown alga gametophyte cells used originate from the alga *Undaria pinnatifida*.

11. The process as defined in claim 2, according to which, during step B), said at least one fatty acid triglyceride comprising from eight to twenty-two carbon atoms is a mixture of fatty acid triglycerides which comprise from eight to ten carbon atoms.

12. The process as defined in claim 3, according to which, during step B), said at least one fatty acid triglyceride comprising from eight to twenty-two carbon atoms is a mixture of fatty acid triglycerides which comprise from eight to ten carbon atoms.

13. The process as defined in claim 2, according to which, during step B), the weight ratio of the weight of brown alga gametophyte cells to the weight of fatty acid triglycerides which comprise from eight to twenty-two carbon atoms is greater than or equal to 2% and less than or equal to 10%.

14. The process as defined in claim 3, according to which, during step B), the weight ratio of the weight of brown alga gametophyte cells to the weight of fatty acid triglycerides which comprise from eight to twenty-two carbon atoms is greater than or equal to 2% and less than or equal to 10%.

15. The process as defined in claim 4, according to which, during step B), the weight ratio of the weight of brown alga gametophyte cells to the weight of fatty acid triglycerides which comprise from eight to twenty-two carbon atoms is greater than or equal to 2% and less than or equal to 10%.

16. The process as defined in claim 2, also comprising a step $A_0$) of preparing said aqueous suspension of brown alga gametophyte cells used in step A) by rehydrating a lyophilizate of brown alga gametophyte cells.

17. The process as defined in claim 3, also comprising a step $A_0$) of preparing said aqueous suspension of brown alga gametophyte cells used in step A) by rehydrating a lyophilizate of brown alga gametophyte cells.

18. The process as defined in claim 4, also comprising a step $A_0$) of preparing said aqueous suspension of brown alga gametophyte cells used in step A) by rehydrating a lyophilizate of brown alga gametophyte cells.

* * * * *